United States Patent
Carner et al.

(10) Patent No.: US 6,332,881 B1
(45) Date of Patent: Dec. 25, 2001

(54) SURGICAL ABLATION TOOL

(75) Inventors: David J. Carner, Fremont; Reynaldo P. Hilario, Sunnyvale; Mahmoud K. Seraj, Mountain View, all of CA (US)

(73) Assignee: Cardima, Inc., Fremont, CA (US)

( * ) Notice: Subject to any disclaimer, the term of this patent is extended or adjusted under 35 U.S.C. 154(b) by 0 days.

(21) Appl. No.: 09/387,889

(22) Filed: Sep. 1, 1999

(51) Int. Cl.$^7$ .................................................. A61I 18/18
(52) U.S. Cl. ................................. 606/41; 606/47; 606/49
(58) Field of Search ................................... 600/374–387, 600/585; 606/41, 33, 45, 46; 607/101, 119, 122, 156

(56) References Cited

U.S. PATENT DOCUMENTS

| | | |
|---|---|---|
| D. 359,354 | 6/1995 | Butter . |
| 4,444,195 | 4/1984 | Gold . |
| 4,681,117 | 7/1987 | Brodman et al. . |
| 5,318,525 | 6/1994 | West et al. . |
| 5,327,905 | 7/1994 | Avitall . |
| 5,336,182 * | 8/1994 | Lundquist et al. ...................... 604/95 |
| 5,354,297 | 10/1994 | Avitall . |
| 5,405,375 | 4/1995 | Ayers et al. . |
| 5,417,208 | 5/1995 | Winkler . |
| 5,423,772 | 6/1995 | Lurie et al. . |
| 5,423,811 | 6/1995 | Imran et al. . |
| 5,433,729 | 7/1995 | Adams et al. . |
| 5,478,330 | 12/1995 | Imran et al. . |
| 5,500,012 | 3/1996 | Bruckner et al. . |
| 5,545,200 * | 8/1996 | West et al. ........................... 607/122 |
| 5,578,007 | 11/1996 | Imran . |
| 5,578,067 | 11/1996 | Ekwall et al. . |
| 5,582,609 | 12/1996 | Swanson et al. . |
| 5,642,736 | 7/1997 | Avitall . |
| 5,643,197 | 7/1997 | Brucker et al. . |
| 5,643,231 | 7/1997 | Lurie et al. . |
| 5,662,697 | 9/1997 | Li et al. . |
| 5,715,817 | 2/1998 | Stevens-Wright et al. . |
| 5,715,818 | 2/1998 | Swartz et al. . |
| 5,782,828 | 7/1998 | Chen et al. . |
| 5,810,802 | 9/1998 | Panescu et al. . |
| 5,823,955 * | 10/1998 | Kuck et al. ........................... 600/374 |
| 5,826,576 | 10/1998 | West . |
| 5,827,278 | 10/1998 | Webster, Jr. . |
| 5,837,001 | 11/1998 | Mackey . |
| 5,843,019 | 12/1998 | Eggers et al. . |

(List continued on next page.)

FOREIGN PATENT DOCUMENTS

19541566A1 * 5/1997 (DE) .............................. A61B/17/39

Primary Examiner—Linda C. M. Dvorak
Assistant Examiner—David M. Ruddy
(74) Attorney, Agent, or Firm—Fitch, Even, Tabin & Flannery (57) ABSTRACT

This is a tool used during open heart or open chest surgery for creating lesions or lines of ablation in tissue to treat atrial fibrillation. It is a relatively short device having a rigid or semi-rigid shaft connected on one end to a handle and on the other end to a more flexible distal tip having one or more electrodes. The distal end of the shaft is angled so to define a first plane of deflection. A deflection mechanism consisting of a pull wire and flat spring housed in a lumen of the tool is manipulable via the handle for deflecting the distal tip in a plane different than the first plane of deflection, allowing direct contact with the curved surface of the tissue, either epicardial or endocardial, to be ablated. The tool may contain fiber optic or other data lines for transmitting data relevant to the patient, and it may be irrigated to cool the tool and the electrodes or to deliver therapeutic fluids to tissue. The tool may also contain temperature sensing device such as a thermocouple or thermistor, which can optionally be configured in a feedback and control system with the irrigation to selectively monitor and control the temperature of the tool or surrounding tissue.

26 Claims, 4 Drawing Sheets

U.S. PATENT DOCUMENTS

| | | | |
|---|---|---|---|
| 5,843,154 | * 12/1998 | Osypka | 607/122 |
| 5,863,291 | 1/1999 | Schaer . | |
| 5,865,800 | 2/1999 | Mirachi et al. . | |
| 5,876,373 | 3/1999 | Giba et al. . | |
| 5,879,295 | 3/1999 | Li et al. . | |
| 5,881,732 | 3/1999 | Sung et al. . | |
| 5,882,333 | * 3/1999 | Schaer et al. | 604/95 |
| 5,885,272 | 3/1999 | Aita et al. . | |
| 5,895,355 | 4/1999 | Schaer . | |
| 5,895,417 | 4/1999 | Pomeranz et al. . | |
| 5,897,529 | 4/1999 | Ponzi . | |
| 5,902,291 | 5/1999 | Houser et al. . | |
| 5,906,590 | 5/1999 | Hunjan et al. . | |
| 5,906,613 | 5/1999 | Mulier et al. . | |
| 5,908,405 | 6/1999 | Imran et al. . | |
| 5,913,854 | 6/1999 | Maguire et al. . | |
| 5,916,209 | 6/1999 | Mick . | |
| 5,916,213 | 6/1999 | Haissaguerre et al. . | |
| 5,916,214 | 6/1999 | Cosio et al. . | |
| 5,921,924 | 7/1999 | Avitall . | |
| 5,928,276 | 7/1999 | Griffin, III et al. . | |
| 5,931,811 | 8/1999 | Haissaguerre et al. . | |
| 5,938,659 | 8/1999 | Tu et al. . | |
| 5,964,757 | * 10/1999 | Ponzi | 606/45 |
| 5,967,978 | 10/1999 | Littmann et al. . | |
| 6,048,329 | * 4/2000 | Thompson et al. | 604/95 |
| 6,080,151 | * 6/2000 | Swartz et al. | 606/45 |
| 6,120,500 | * 9/2000 | Bednarek et al. | 606/41 |
| 6,156,031 | * 12/2000 | Aita et al. | 606/33 |

* cited by examiner

SURGICAL ABLATION TOOL

TECHNICAL FIELD

This invention generally relates to the treatment of cardiac arrhythmia and atrial fibrillation. In particular, this invention is a surgical ablation tool for treating atrial fibrillation by creating lesions in cardiac tissue during open heart or open chest surgery.

BACKGROUND

Atrial fibrillation (AF) is characterized by the irregular and very rapid beating of the heart's atrial chambers and results when the normal electrical conduction system of the atria malfunctions, leading to irregular and chaotic electrical signals. During AF, the regular pumping action of the atria is replaced by irregular, disorganized and quivering spasms of atrial tissue. These spasms may lead to reduced blood flow, blood clots, stroke and even death. This malfunction results in the failure of the atria to fill the ventricles completely and, consequently, the failure of the heart to pump adequate amounts of blood to the body. Once AF becomes symptomatic, it is typically associated with significant morbidity related to reduced blood flow. Often, the greatest concern is that the reduced cardiac output can lead to blood pooling in the atria and the formation of blood clots. Blood clots in the left atrium can dislodge and travel through the bloodstream to the brain, resulting in stroke and even death.

In the United States, AF currently affects an estimated two million people, with approximately 160,000 new cases being diagnosed each year. About 1.5 million outpatient visits and more than 200,000 patient admissions per year in the United States are associated with AF. AF is responsible for over 70,000 strokes each year in the United States alone; the annual cost of treating these patients is more than $3.6 billion. The cost of drug treatment for AF alone is estimated to be in excess of $400 million worldwide each year.

Current AF treatments are directed to reestablishing a normal heartbeat and preventing stroke, and are primarily supportive and palliative rather than curative. Antiarrhythmic and anticoagulant drugs (such as sodium and calcium channel blockers) or drugs which reduce the Beta-adrenergic activity are the most common treatment for AF. These drugs are used to control AF by restoring the heart's natural rhythm and limiting the natural clotting mechanism of the blood. However, antiarrhythmic drug therapy often becomes less effective over time, with approximately half of the patients eventually developing resistance. In addition, antiarrhythmic drugs can have severe side effects, including pulmonary fibrosis and impaired liver function.

Another palliative procedure for AF is external cardioversion, or the application of strong electrical current under general anesthesia. This treatment is usually only effective for a limited period of time as well. Implantable atrial defibrillators are being investigated to detect the onset of AF internally and then deliver an electrical shock to convert the heart back to normal rhythm. Although the preliminary results of clinical studies indicate that this approach may be feasible, AF is not cured with this approach. There are also significant problems with this treatment, including pain tolerance, reversion to AF and creation of ventricular tachycardia as a result of the electrical shock.

Purposeful destruction of the Atrio-Ventricular (AV) node followed by implantation of a pacemaker is typically a treatment of last resort for AF patients, but does not cure or treat the AF itself Since atrial function remains poor following the procedure, chronic anticoagulant therapy is generally required.

Another therapy for AF is an open heart operation. In a technique known as the "maze" procedure, a surgeon makes several slices through the wall of the atrium with a scalpel and then sews the cuts back together, creating a scar pattern. The scars isolate and contain the chaotic electrical impulses to control and channel the electrical signal emanating from the SA node.

This open heart operation is expensive and associated with long hospital stays, high morbidity and mortality. Although this approach is not commonly used because it is highly invasive, containing the movement of the chaotic impulses in the atrium through scar creation is generally considered effective in controlling AF.

An alternative to open heart or open chest surgery is a minimally invasive treatment technique in which radiofrequency (RF) ablation catheters are used to form thin, continuous linear scars in various locations in the atria. This procedure has the promise of safely treating AF with significantly reduced trauma.

Although such RF ablation catheters have proliferated in recent years, the technique is still in its infancy. Difficulties associated with clearly imaging and accessing various portions of the cardiac anatomy to create the desired lesions exemplify some of the shortcomings of this treatment that still have yet to be overcome.

One treatment combines the advantages of the open heart "maze" procedure and RF catheter-based treatment such that lesions are created in an open heart environment with one or more RF electrodes and not the surgeon's scalpel. However, there is a significant unresolved need to provide a tool adequate to perform such a procedure in a safe, effective, and reliable manner.

What is needed is an ablation device which can be used as a surgical tool that assures adequate tissue contact prior to ablation but which is flexible enough to create both straight and curved lines of conduction block, etc. in endocardial and epicardial applications.

SUMMARY OF THE INVENTION

This invention is directed to a surgical ablation tool suitable for forming linear lesions on cardiac tissue during open heart or open chest surgery to treat atrial fibrillation and flutter.

The deflectable surgical ablation assembly includes a main body comprising a semi-rigid elongate member defining a lumen and having a distal end and a proximal end. This member forms an angle at its distal end, typically between 90 degrees and 180 degrees, which defines a first plane of deflection.

A multilumen flexible tip is distally fixed to the main body and houses a deflection mechanism for deflecting the tip about a second plane of deflection, typically substantially perpendicular to the first plane, and at least one electrode disposed on an outer surface of the tip. The deflection mechanism consists of a pull wire attached to a linear spring. The tip is capable of deflecting to the point that the tip distal end physically contacts a more proximal portion of the ablation assembly. A nonactive atraumatic tip or cap is typically fixed distally on the flexible tip as well.

A handle is proximally connected to the main body for manipulating the pull wire. The handle can include a connector for transmitting electromagnetic energy between the tip and a remote device, such as an electrocardiogram recording system, a radiofrequency power supply, and the like.

Optionally, the tool distal tip can have one or more apertures through the tip exterior surface and connected to a lumen defined in the tip. Fiber optic or other data transmission cables can be disposed in the main body for transmitting data related to the patient from an outside device.

The assembly may also be irrigated to deliver cooling fluids to the tip and the electrode or electrodes, and one or more temperature sensing devices can be incorporated into the device on the tip as well.

These and other advantages of the invention will become more fully apparent when the following detailed description of the invention is read in conjunction with the accompanying drawings.

DESCRIPTION OF THE INVENTION

This invention includes a surgical ablation catheter, or tool, which is most suitable for use in ablating cardiac tissue during open heart or open chest surgery. This relatively short device (in comparison to conventional ablation catheters) has a handle connected to an angled rigid or semi-rigid shaft which terminates in a deflectable active electrode region. The electrode region is deflectable in a plane generally perpendicular to the plane of deflection defined by the distal end of the shaft. One or more electrodes are disposed on the active electrode region for ablating cardiac tissue. The handle is useable for maneuvering the tool and deflecting the active electrode region.

In general, the tool of the invention can be used in a variety of applications, including open heart surgery (for endocardial lesion formation) and open chest surgery (for epicardial lesion formation). The shaft of the catheter is useful to ensure the active electrode region adequately contacts the tissue of interest so that lesions can be created as safely and effectively as possible. Due to the unique shape and deflection capability of the tool, one particularly useful application of this catheter is in creating both straight and curved lines of conduction block encircling the pulmonary veins, simulating the conventional surgical "maze" procedure.

The tool is best used during open heart surgery, for example during mitral valve replacement. During use, the left atrium, right atrium, or both are exposed using conventional techniques for visual placement of the catheter. Various tissue can be adequately reached by the tool. Typically the tool will best be used around the pulmonary veins, various septal lines and various right atria lines (including, e.g., Interior Vena Cava (IVC) to Superior Vena Cava (SVC), Isthmus, etc.).

Figure 1:
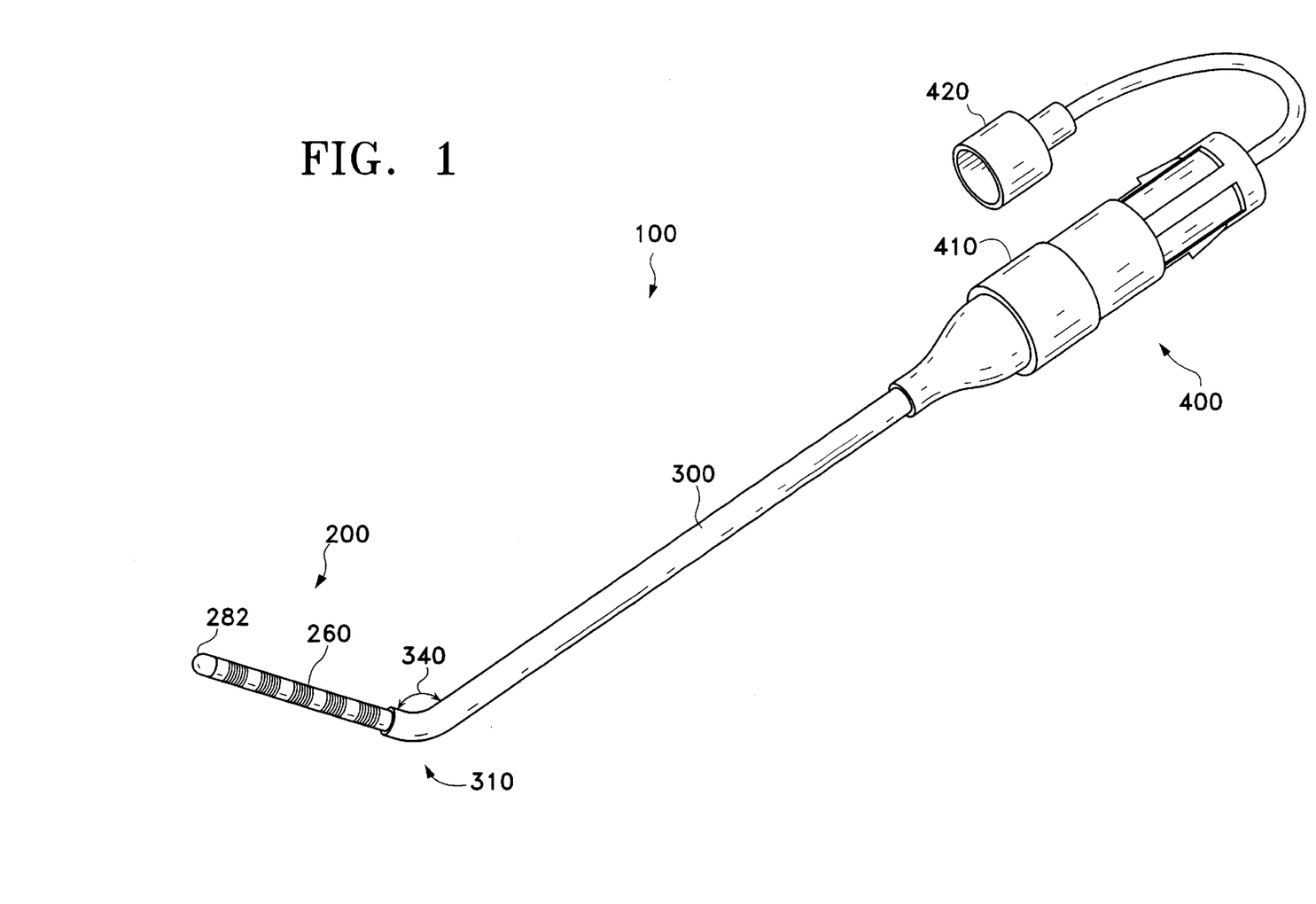
FIG. 1 is a perspective of the surgical ablation tool of the present invention.

Turning now to the drawings, FIG. 1 depicts a short, agile and responsive catheter or tool suitable for surgically ablating cardiac tissue. In this aspect of the invention, tool 100 comprises handle 400, shaft 300, and distal flexible electrode region or tip 200.

Deflection handle 400, generically shown in FIG. 1, is designed so to allow the surgeon to grip and manipulate tool 100 with maximum ease. It includes a control knob 410 or the like for manipulating the flexible distal electrode region 200. Handle 400 may optionally contain a port or connector 420 for coupling the catheter 100 with one or more number of external devices such as, e.g., an electrocardiogram recording system, an RF power supply, or a remote visualization system (via a fiber optic or traditional data link). In general, any handle suitable for interfacing with the user and allowing manipulation of the catheter 100 is within the scope of the invention. For example, the handle described in pending U.S. patent application Ser. No. 09/001,249, entitled "Deflectable Guiding Catheter" to Qin et al., filed Dec. 30, 1997, the contents of which are herein incorporated by reference in their entirety, can be used in the present invention.

Connected to the handle 400 is main body or semi-rigid shaft 300 which comprises the majority of the length of ablation tool 100. Shaft 300, which is rigid or semi-rigid in comparison to distal tip 200, has a proximal end, a distal end, and a lumen (not shown in FIG. 1). The distal end of shaft 300 is characterized by the presence of an angled shaft region 310. Angled region 310 defines an angle 340 generally greater than about 90 degrees so that the entire distal electrode region 200 is angled with respect to the rest of catheter 100 as shown in FIG. 1. This angle 340 defines a plane of deflection that allows the user to access areas in the cardiac anatomy that are otherwise difficult to reach.

Flexible distal tip or active electrode region or tip 200 is disposed distally of shaft 300. Distal tip 200 is characterized by its higher flexibility in comparison to that of rigid or semi-rigid shaft 300, its angled disposition relative to the majority of shaft 300, its manipulability for deflection, and the presence of at least one electrode 260. As is shown in FIG. 1, five such electrodes 260 are preferably disposed on tip 200. Also shown is an atraumatic nonactive distal tip or cap 282 disposed on the distalmost end of electrode region 200. These and other features of the surgical ablation tool 100 of the invention will now be discussed below in greater detail.

Figure 2:
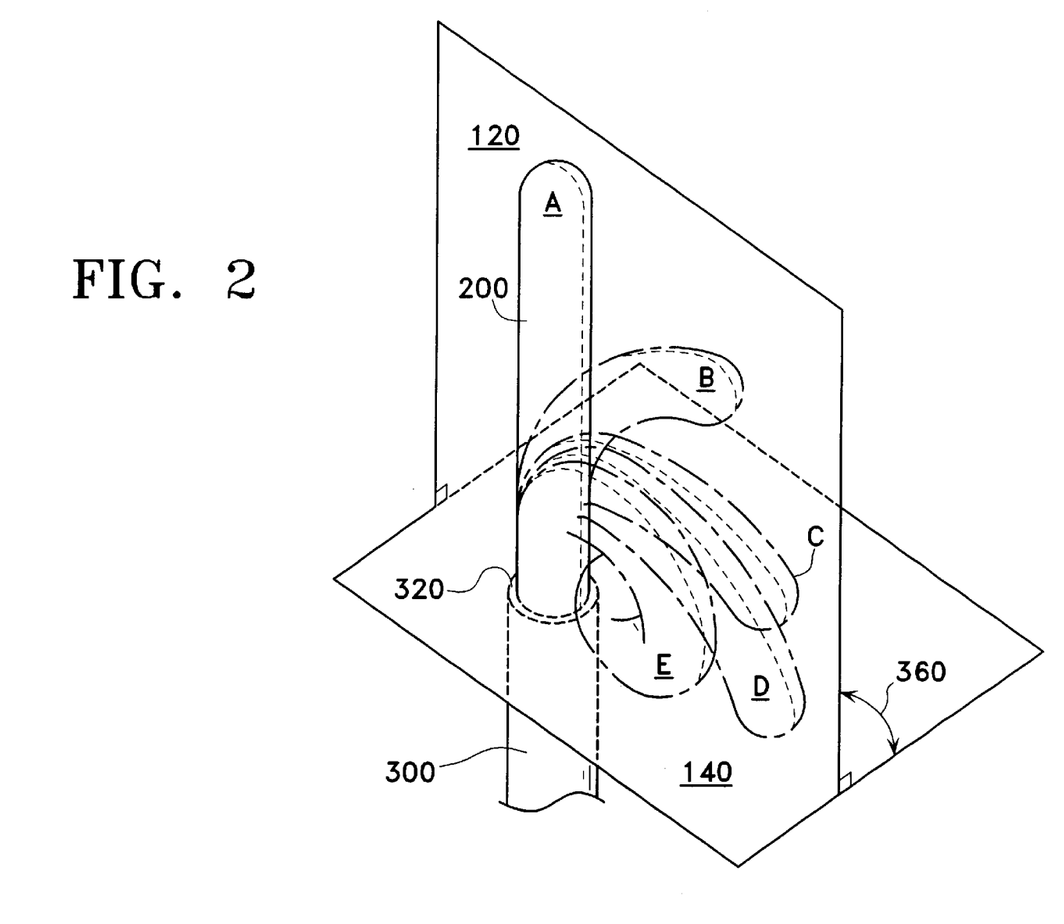
FIG. 2 is a schematic of the distal portion of the tool detailing in phantom deflection of the electrode region.

Turning now to FIG. 2, the portion of catheter 100 distal to bend 310 is shown. This Figure demonstrates the shape and plane of deflection of distal tip region 200 upon manipulation.

Electrode region 200 is schematically shown in FIG. 2 in five different positions for purposes of example only. As can be seen, in its straight, undeflected position A, tip 200 extends distally in the same direction as the portion of shaft 300 distal of bend 310. The tool 100 can be configured to default to this position such that when knob 410 (or other manipulation device) is in a resting position, tip 200 will assume a position approximating position A as depicted in FIG. 2. Of course, it is within the scope of this invention that the catheter 100 can be manufactured or set by the user (such as via a locking mechanism or the like) so that distal end 200 defaults to any position into which tip 200 is capable of deflection. The various positions B, C, D, and E are shown in phantom to demonstrate the progressively more severe angles of deflection for tip 200 upon manipulation of the deflection mechanism. The most severe deflection in FIG. 2 is shown in position E, where tip 200 is deflected such that the distal end of tip 200 may contact tool 100 at a distal portion of shaft 300, forming a closed loop.

Note that tip 200 deflects in FIG. 2 in a gentle U-shaped mode. Depending upon the configuration of the deflection mechanism, any number of different forms can be realized by tip 200 within the scope of the invention. This enables tip 200 to adequately contact tissue having a variety of different surface shapes, allowing the tool to be used in various difficult-to-reach areas of the heart.

It is generally desirable that distal electrode tip 200 be deflectable in a single plane 120. As seen in FIG. 2, plane 120 is generally perpendicular to a plane 140 defined by, and parallel to, the distal surface 320 of shaft 300. Of course, it is not necessary to this invention that planes 120 and 140 be perpendicular to each other as shown in FIG. 2; the angle between planes 120 and 140 can vary from zero degrees to 180 degrees. However, we have found that it is generally preferable that planes 120 and 140 be different; i.e., that they be oriented to one another at some angle greater than zero degrees and less than 180 degrees. More preferably, these planes are disposed at an angle of between 70 and 110 degrees to one another. Most preferable is an angle of about 90 degrees.

Figures 3, 4, 5:
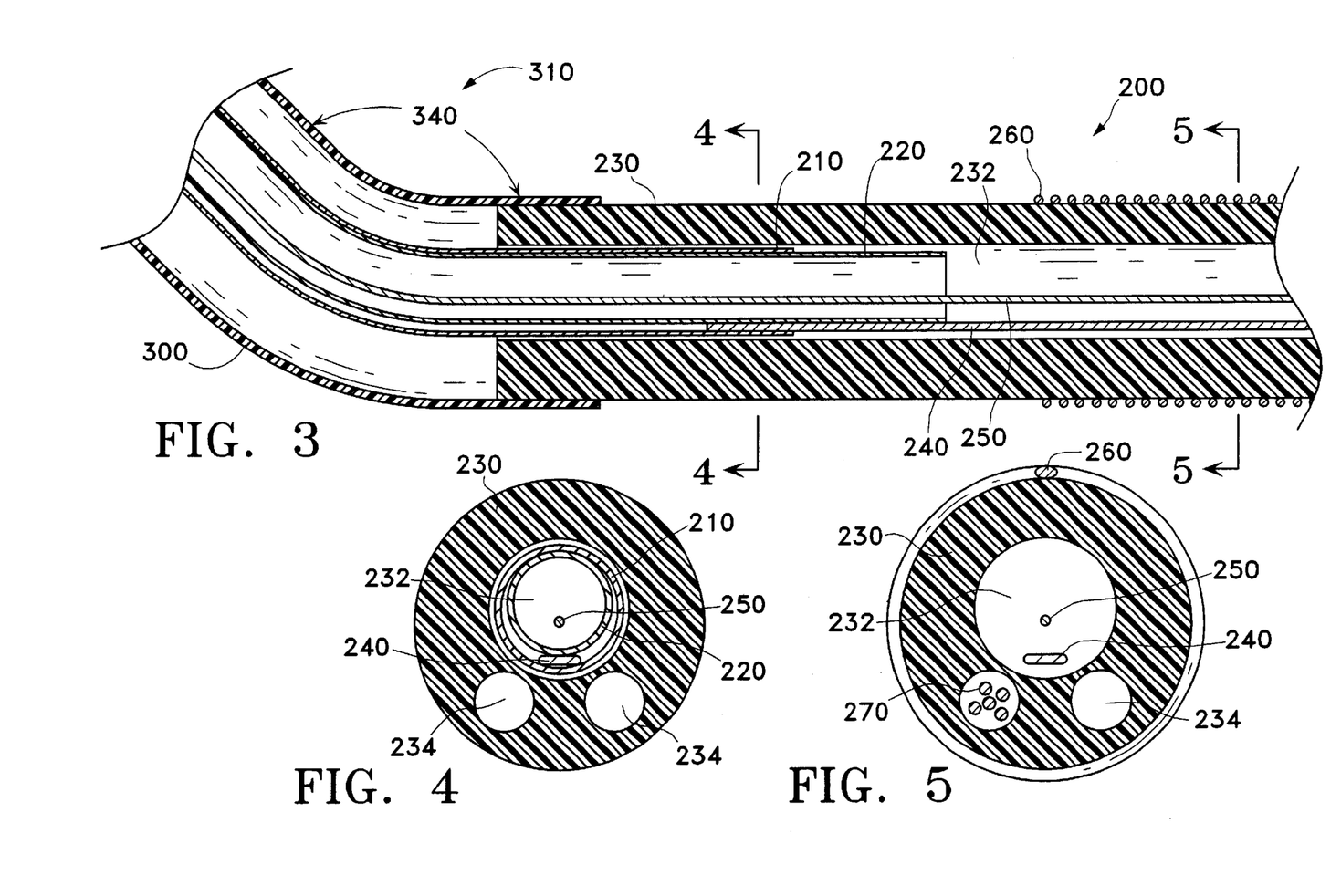
FIG. 3 is a longitudinal cross section of a proximal portion of the tool electrode region detailing the deflection mechanism and interior structure.
FIG. 4 is a transverse cross section of a proximal portion of the tool electrode taken along the lines 4—4.
FIG. 5 is a transverse cross section of a more distal portion of the tool electrode taken along the lines 5—5.

Turning now to FIGS. 3–5, various cross sections of the catheter 100 are shown in the vicinity of the junction between shaft 300 and distal electrode region or tip 200.

FIG. 3 displays this region of catheter 100 in longitudinal cross section. First hypotube or shaft 300 is shown at bend or elbow 310 defining an angle 340. As previously discussed, angle 340 is generally greater than 90 degrees. It is preferable that angle 340 be between about 80 degrees and 180 degrees; more preferably between about 90 degrees and 120 degrees, and most preferably about 110 degrees.

First hypotube 300 is relatively short, having a total length generally between about 2 and 20 inches. This length allows a physician user to employ catheter 100 easily during surgery. It is preferable that the total length of shaft 300 be between about 4 and 8 inches; most preferably about 6 inches. The particular length of shaft 300 will depend on the particular application and conditions under which ablation tool 100 is employed.

First hypotube shaft 300 has an outer diameter of between about 0.05 and 0.20 inch; more preferably, between about 0.09 and 0.15 inch; most preferably about 0.11 inch. It generally has a wall thickness of between about 0.01 and 0.05 inch, more preferably between about 0.02 and 0.03 inch; most preferably about 0.024 inch.

Although we refer to the term "hypotube" throughout the specification, the invention is not so limited. Any appropriate surgical tubing having the correct physical and structural characteristics (e.g., strength, stiffness, etc.) is suitable.

Shaft 300 can be made from any material suitable to meet the performance requirements of catheter 100. Preferably, hypotube 300 is stainless steel. It also can be made from, in whole or in combination, metals such as iridium, platinum, palladium, rhodium, gold, tungsten, titanium, tantalum, nickel, and alloys thereof. Shaft 300 may also be made from any number of suitable relatively rigid or semi-rigid polymers, alloys or mixtures thereof. For instance, shaft 300 tubing may be a polyamide (such as the Nylons), high density polyethylene (HDPE), polypropylene, polyvinylchloride, various fluorocarbon polymers (PTFE, FEP, vinylidene fluoride, etc.), polysulfones, or the like. Blends, alloys, mixtures, copolymers and block copolymers of these materials are also suitable if desired.

As long as the hypotube 300 is capable of maintaining a relatively rigid or semi-rigid shape in comparison to distal tip 200 and can withstand the torsional, compressive, and bending stresses imposed during use with integrity, any suitable material can be used.

A second, smaller hypotube 210 houses the pull wire and linear spring making up the operable portion of the deflection mechanism for tip 200. Hypotube 210 is affixed by, e.g., soldering, welding, adhesives such as glue, or the like, and preferably by brazing, to the inner surface of shaft 300 in a proximal portion of shaft 300 (not shown). As shown in FIGS. 3 and 4, however, second tube 210 is disposed in the center of the hypotube 300 lumen and is not affixed to the hypotube 300 distal end. Second hypotube can be made of any of the materials described above with respect to first hypotube or shaft 300. Second hypotube tube will generally have an outer diameter of between about 0.01 and 0.05 inch; preferably between about 0.02 and 0.04 inch; most preferably about 0.032 inch. Its inner diameter defines a wall thickness of between about 0.005 and 0.018 inch; more preferably between about 0.01 and 0.015 inch; most preferably about 0.012 inch. When proximally affixed to the inner wall of shaft 300, hypotube 200 extends distally out of first hypotube or shaft 300 by approximately 1 to 5 mm; preferably about 3 mm.

A third even smaller tube 220 is disposed in the lumen of second hypotube 210 and distally extends between about 0.5 and 7 mm, preferably about 5 mm, out of the distal end of tube 210. Tube 220 is preferably a polyimide, but may also be made from other polymers such as PEEK and those discussed above. Tube 220 may also be a metal or metal alloy as discussed above. Typically, third tube 220 has an outer diameter of between about 0.01 and 0.03 inch, preferably between about 0.012 and 0.02 inch, and most preferably about 0.017 inch. Its wall thickness desirably is in the range of 0.001 and 0.005 inch, and is preferably about 0.002 inch.

Disposed between the outer surface of third tube 220 and the inner surface of second tube 210 lies linear spring or wire 240. As can be seen in FIG. 3, spring 240 extends into the lumen of hypotube 210 where it is affixed to tube 210 by soldering, brazing, adhesive or any suitable means. Typically the proximal end of spring 240 will extend between about 1 and 7 mm into second hypotube 210, preferably about 5 mm. Flat wire 240 is preferably comprised of a metal or metal alloy such as those previously described, and is preferably stainless steel. Spring 240 may also be made from a nickel-titanium alloy, commonly known as nitinol, for its shape memory characteristics, and may also be polymeric or a combination of a polymer and metal. As will be discussed in detail below, linear spring 240 acts to provide the tension and stiffness needed for the deflection mechanism when used in conjunction with pull wire 250.

Linear spring 240 is generally in the form of a solid, flat, rectangular ribbon or wire having a rectangular transverse cross-section as shown in FIGS. 4 and 5. Spring 240 may be tapered along its length in the distal direction. The taper may be just in the short transverse dimension or both the short and long transverse dimensions. Such a configuration allows the spring 240 and pull wire 250 to effectively deflect tip 200 in plane 120 as will be described in detail below. Typically, wire spring 240 will have a width of between about 0.005 and 0.025 inch, more preferably between about 0.01 and 0.2 inch, and most preferably about 0.015 inch. The thickness of spring 240 will typically be between about 0.002 and 0.008 inch; more preferably between about 0.004 and 0.007 inch, and most preferably about 0.006 inch. Of course, other cross-sectional shapes for spring 240, such as square, circular, elliptical, etc. are within the scope of this invention. Spring 240 may also take on a variety of forms, such as a reinforced coil or braid, or it may be a solid ribbon or wire surrounded by a coil or braid.

Pull wire or deflection control line 250 is shown in FIGS. 3–6 as a thin, flexible wire, cable, or ribbon having a preferably round cross-section and slidably disposed in handle 400 through shaft 300, tube 210, third tube 220, and into distal tip 200. Although not shown in the figures, line 250 is proximally affixed to handle 400 and can be moved axially within the various components of tool 100 via tension to deflect the deflectable linear spring 240, which in turn deflects distal tip 200 as shown in phantom in FIG. 2. The radius of curvature of the distal electrode tip 200 is controlled by the tension applied to pull wire 250. Note that pull wire line 250 extends through third tube 220 as shown in FIGS. 3 and 4 and continues distally through shaft 300 in the large lumen 232 of multilumen tubing 230.

Pull wire 250 is preferably comprised of a metal or metal alloy as discussed above. It also may be polymeric. Preferably pull wire 250 is made of stainless steel, but may also be made from a nickel-titanium alloy, commonly known as nitinol, for its shape memory characteristics. Other cross-sectional shapes for wire 250, such as square, rectangular, elliptical, etc. are within the scope of this invention. Further details of spring 240 and pull wire 250 and their operation will be discussed below in conjunction with FIG. 6.

Connected by insertion into the lumen at the distal end of shaft 300 and extending distally to the end of catheter 100 is multilumen tubing 230. This component makes up the primary structure of distal electrode region 200.

Multilumen tubing 230 will typically be polymeric as described above. An especially desirable material is, however, an extruded polyether block amide of the type sold by Atochem North America, Inc., under the trademark PEBAX. Typically, tubing 230 is between about 20 and 70 mm in length, preferably between about 35 and 55 mm; most preferably about 45 mm. Its outer diameter should be sufficient to fit within the inner lumen of shaft 300 as shown in FIG. 3, preferably between about 0.06 and 0.12 inch; most preferably about 0.09 inch.

Tubing 230 and shaft 300 are preferably joined by an adhesive or other suitable means. Most preferred is an adhesive sold by Dymax Corp. of Torrington, Conn. under the trademark DYMAX. Also preferred are a variety of medical grade adhesives manufactured and sold by Loctite Corp. of Rocky Hill, Conn.

Although FIG. 3 depicts multilumen tubing 230 connecting to the distal end of shaft 300 by insertion into the shaft 300 lumen, other suitable means for connecting multilumen tubing 230 and shaft 300 are within the scope of the invention.

The multilumen tubing 230 depicted in FIGS. 4 and 5 contains one primary lumen 232 and two secondary lumen 234 asymmetrically arranged in the pattern as seen. Such asymmetry allows for easier deflection of distal electrode region 200 as the pull wire/spring deflection mechanism is offset from the tubing's 230 central axis (not shown).

At the location depicted in FIG. 4, primary lumen 232 houses second hypotube 210, third tube 220, flat linear spring 240, and pull wire 250. Secondary lumen 234 are vacant in this section of tool 100.

At the cross-section shown in FIG. 5, primary lumen does not house the various other tubes but still carries unattached spring 240 and pull wire 250. One or both of secondary lumen 234 may carry one or more signal wires 270, each of which is connected to an electrode 260 as discussed below.

Of course, the configuration at the cross-sectional locations depicted in FIGS. 3 through 5 is merely one example of a variety of configurations possible for the inventive device. For example, the interior lumens of multilumen tube 230 can vary in number, diameter, and orientation with respect to each other. In addition, the lumens may house various other elements, e.g., fiber optic lines, data transmission lines, power leads, etc. They may also be utilized to transport fluids such as saline or air for cooling of the electrodes or for dispensation to the tissue of interest through weeping ports and the like. In addition, it is within the scope of this invention that the deflection mechanism comprised of the various elements described herein may be housed largely in the distal tip 200 as shown, largely in shaft 300, or in both sections.

Figure 6:
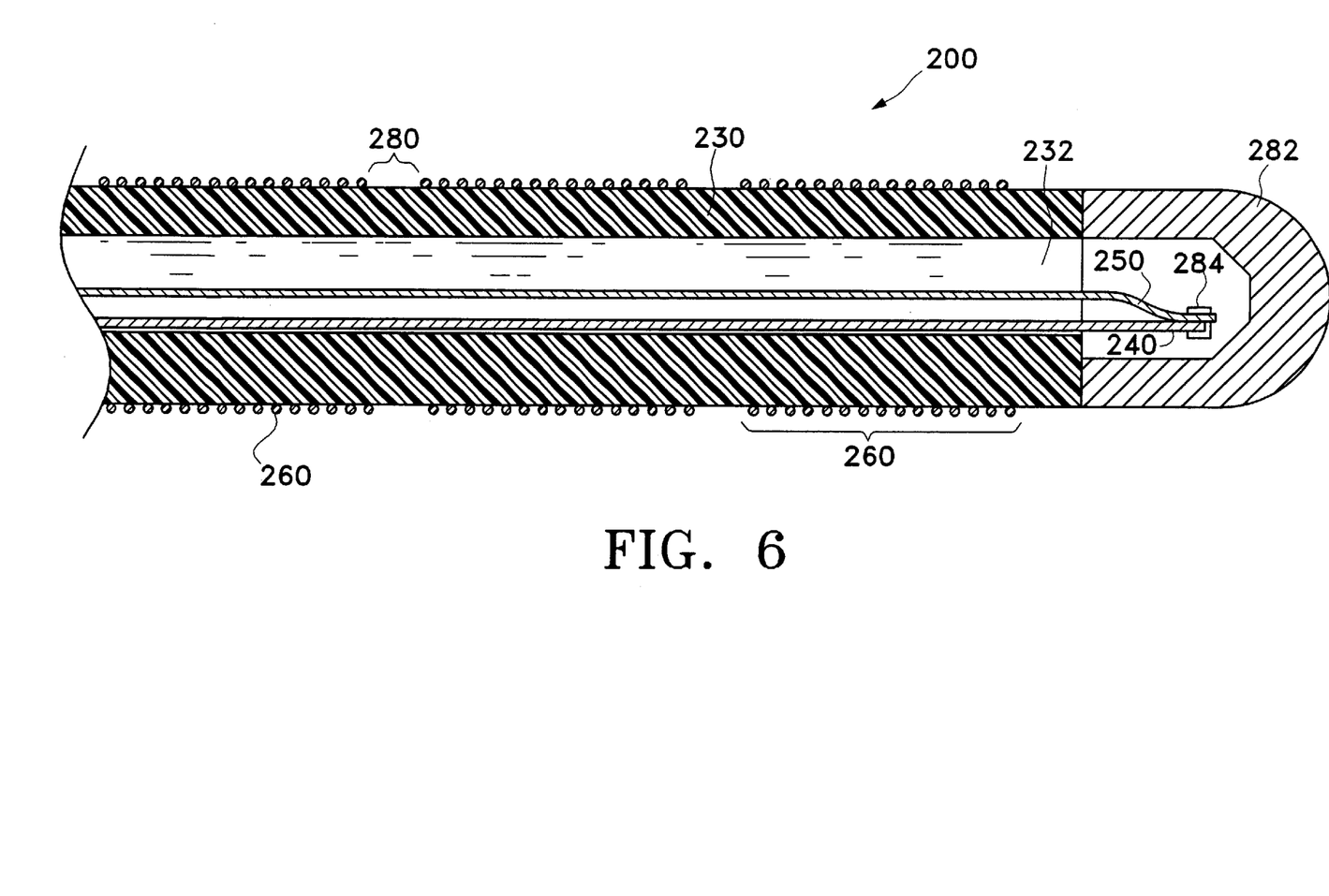
FIG. 6 is a longitudinal cross section of a distal portion of the tool electrode region.

As shown in FIGS. 2, 3, and 6, ablation electrodes 260 are disposed around multilumen tubing 230 in distal tip 200. These electrodes 260 are for delivering electromagnetic, and preferably radiofrequency, energy directly to cardiac or other tissue of interest. In the embodiment shown in these figures, five such ablation electrodes are so disposed and evenly spaced along the length of distal tip 200.

The electrodes 260 are made up of individual metal wires, cylindrical bands, helical coils, arcuate bands or ribbons and the like. Each electrode wire has a diameter between about 0.001 and 0.010 inch, preferably between about 0.003 and 0.007 inch, and most preferably about 0.005 inch. When wound around tubing 230 in tip 200, each electrode 260 formed by the wires is typically between about 3 and 9 mm long, and preferably between about 4 and 7 mm long; most preferably about 6 mm long. Electrodes 260 (and signal wires 270) are preferably constructed of any appropriate electrically conducting metal or metal alloy; e.g., platinum, copper, etc., or their alloys.

Each electrode 260 may be joined by welding, brazing, etc., and preferably by soldering, to a metal signal wire 270. Preferably, but not necessarily, signal wires 270 are of the same cross-sectional shape and diameter as the wires making up electrode 260. Five such wires (one for each electrode) are shown in cross section in FIG. 5 as disposed in one of secondary lumen 234 of multilumen tube 230. Each of the signal wires 270 is inserted into lumen 234 during tool 100 assembly through a small hole (not shown) from lumen 234 through the body of tube 230 and out an exterior wall of multilumen tube 230. In this way, signal wires are routed from each electrode 260 into secondary lumen 234 distally through the lumen of shaft 300 into handle 400 where they are eventually attached, via connector 420 or the like, to an electromagnetic power source (not shown).

Electrodes 260 are shown in FIG. 6 as separated from one another by a spacing 280. Preferably, and in the configuration presented in FIGS. 1–6, this spacing 280 is between about 1.0 and 2.0 mm, most preferably about 1.5 mm. Of course, the width of the particular spacing between any two electrodes can be uniformly higher or lower or even vary along the length of a given electrode region 200, depending upon the particular configuration chosen, whether thermocouples are used, etc.

Each electrode 260 is secured to the outer surface of multilumen tubing 230 by an adhesive, preferably the ultraviolet light-curable adhesive sold under the trademark LOC-TITE Product 3341, which is manufactured by Loctite Corp. of Rocky Hill, Conn. Typically, although not necessarily, adhesive is applied to the edges of each electrode 260 in the proximity of spacing 280. When ultraviolet adhesive such as UV 3341 is used, it is cured by exposing the applied adhesive to a source of ultraviolet light as is well known in the art. The electrodes can also be fixed to tubing 230 via a variety of other adhesives or methods.

Once the electrodes are secured to tubing 230 in their desired configuration, a polymeric layer may be bonded to the multilumen-electrode combination in such a configuration so to present the multilumen tubing 230 with an electrically and thermally insulative surface while still allowing for direct contact between the windings of the electrodes and target tissue for ablation. Preferable are the polyethylene polymers; especially preferred is an ethylene-vinyl acetate copolymer resin sold by the DuPont Corporation of Wilmington, Del. under the trademark ELVAX. Such a polymeric layer is used to insulate the conductor wires inside the shaft and handle.

Of course, the five electrode configuration of tip 200 is but one of many available for the invention. The number of electrodes, the electrode length, tip length, and spacing between electrodes may all be varied to accommodate various cardiac or other anatomy for the application of interest.

Turning now to the distal end of the device, FIG. 6 depicts flat linear spring 240 and pull wire 250 extending the length of the distalmost section of tip 200 and terminating at band 284. Preferably, band 284 comprises a metal or alloy such as platinum, tantalum, titanium, nickel, tungsten, stainless steel, gold, etc. or their alloys. Especially preferred is platinum and its alloys.

As seen in the cross-section shown in FIG. 6, band 284 is preferably a ring or like structure that encircles both spring 240 and wire 250 and is affixed to both via solder or other joining method or medium. Where linear spring 240 has a rectangular cross section (as discussed above in conjunction with the embodiment shown in FIGS. 4 and 5), band 284 preferably helps to position the pulling wire 250 along the center of the wide dimension of spring 240.

Preferably, band 284 is affixed, such as by soldering, welding, brazing or the like such that the distalmost end of pulling wire 250 extends distally of band 284, while the distalmost end of spring 240 does not. Of course, this is but one of many possible configurations for this portion of the device.

The distalmost end of the tool terminates with an atraumatic cap 282 as shown in FIGS. 1 and 6. Tip 282 preferably comprises a metal such as platinum, tantalum, titanium, nickel, tungsten, stainless steel, gold, etc. or their alloys. Preferred is stainless steel. The primary function of tip 282 is to provide a smooth and rounded structure to the distal end of the tool so to prevent damage or trauma to tissue during use. Tip 282 is affixed to the distalmost end of multilumen tubing 230 by any suitable means. It is preferably fixed by an adhesive sold by Dymax Corp. of Torrington, Conn. under the trademark DYMAX. Cap 282 may be active; i.e., it may transmit ablative RF energy to tissue as do the electrodes.

It should be noted that the dimensions and materials disclosed above with respect to the various components shown in each of the Figures are exemplary only. It is expressly within the scope of this invention to vary the length, diameter, wall thickness, material compositions, etc. of the components of surgical tool 100 so to meet any needed manufacturing and functional requirements. For example, shaft 300 is shown to have a generally linear shape proximal to the elbow or bend 310 as seen in FIG. 1. Shaft 300 need not have this strict configuration. Not only can the angle 340 of elbow or bend 310 vary, other elbows or bends (not shown) can be included in shaft 300 so that it takes on a more nonlinear profile. Such additional bends can be located at any position along the length of catheter shaft 300 from the handle 300 to the distalmost end of the shaft beyond bend 310.

Several alternative embodiments and configurations are within the scope of this invention. For instance, one or more thermocouples, thermistors or other temperature sensing device can be incorporated into the tool 100 to allow for temperature monitoring of the electrodes, the tool, or of tissue during the ablation process; likewise, such devices may be used in a more sophisticated feedback and control system as is well known in the art. It is preferred that if thermocouples are used, one or more T-type thermocouples be disposed on the surface of multilumen tubing 230 on tip 200 in the interelectrode spaces 280.

Another feature that may be combined with the structure disclosed above, singly or in part, is an irrigation system for bathing the distal tip 200 (e.g. electrodes, multilumen tube) in fluids such as saline so to minimize the formation of thrombi and the effects of impedance rise and tissue charring during ablation.

As discussed above, one way to incorporate such an irrigation system in this tool 100 is to introduce a fluid, such as a liquid or air, into one of the lumen of the multilumen tubing 230 which removes built-up heat from electrodes 260 through the body of multilumen tubing 230. Such an irrigation feature can be used in a feedback and control system based upon the temperature sensed by the temperature sensing means.

For instance, a fluid can be introduced into one of secondary lumen 234, which lumen 234 can then either be sealed or connected to a flushing or recirculation system to pass cooling fluid therethrough. Alternatively, weeping irrigation systems or systems in which one or more electrodes are directly sprayed with cooling fluid are within the scope of the invention. Cooling irrigation systems such as those described in U.S. Pat. No. 5,863,291 to Schaer, the entirety of which is hereby incorporated by reference, are for example suitable for use in the present invention (modified, of course, to account for structural differences).

In addition, the inventive device may be modified to deliver fluids such as cardioplegic materials, e.g., solutions of iced saline, KCl, lidocaine, procaineamide hydrochloride and the like to the cardiac or other tissue of interest during surgery.

Fiber optics or other traditional (i.e. copper) transmission wires may also be used in conjunction with the tool 100 to transmit data from the distal end 200 of the catheter to any number of devices, such as diagnostic, recording, viewing, or other equipment. For instance, fiber optic lines can occupy any of the lumen 232, 234 in multilumen tubing 230 and extend to the end of tool 100 at atraumatic tip 282.

In a preferred application, a surgeon opens the chest wall and exposes the chest cavity in the vicinity of the heart. The assembly of the invention as shown in FIGS. 1–6 is introduced to the exterior surface of the heart (when epicardial lesions are to be formed) or the exposed surfaces of the interior of the heart, such as the left and/or right atria (when endocardial lesions are to be formed). Via manipulation of the handle, the shape of the distal tip 200 is modified by the deflection mechanism so that at least one, but preferably all, of the electrodes 260 are placed in direct contact with the tissue to be ablated. The rigid or semi-rigid shaft 300 serves to transmit axial forces applied by the surgeon via handle to assure adequate contact between the tip 200 and the tissue to be ablated. Adequate contact with the target tissue can be assured by using the tool in a pushing motion, similar to that used when employing a branding iron. Tissue contact can also be assured by using the catheter in a pulling motion, which utilizes the top of the active electrode region to reach tissue that might otherwise be difficult to access.

Next, the electrodes are energized by RF energy transmitted from an RF power source through connector 420 and the electrode signal wires 270, causing ablation and cauterization of the target tissue. Typically, the RF current is directed to one or two electrodes at the most distal end of the EP device to perform the first ablation and then continue proximally one or two electrodes at a time until a linear ablation of desired length is obtained in the atrial chamber. This reduces the overall power requirements for the assembly. The electrodes 260 heat up due to the conductive heat transfer from the tissue being ablated and the linear lesions are created as needed.

This invention has been described and specific examples of the invention have been portrayed. The use of those specific examples is not intended to limit the invention in any way. Additionally, to the extent that there are variations of the invention which are within the spirit of the disclosure and yet are equivalent to the inventions found in the claims, it is our intent that those claims cover those variations as well.

We claim as our invention:

1. A deflectable surgical ablation assembly for forming ablations during open heart or open chest surgery, said deflectable surgical ablation assembly comprising:
   a main body comprising a rigid or semi-rigid elongate member capable of transmitting axial forces applied by a surgeon to tissue being ablated, and defining a lumen and having a distal end and a proximal end, the member having a preformed angle at the distal end which defines a first plane of deflection; and
   a flexible tip disposed distally of said main body, said tip housing (1) a deflection mechanism for deflecting the tip about a second plane of deflection different than said first plane and (2) at least one electrode disposed on an outer surface of the tip.

2. The assembly of claim 1 wherein said first plane of deflection is generally perpendicular to said second plane of deflection.

3. The assembly of claim 1 additionally comprising a handle disposed proximally of said main body, wherein said handle is rigidly connected to the main body and effective for transmitting axial forces applied by a surgeon to tissue being ablated.

4. The assembly of claim 1 additionally comprising a connector disposed on said handle for transmitting electromagnetic energy between said tip and a remote device.

5. The assembly of claim 4 wherein said remote device is an electrocardiogram recording system.

6. The assembly of claim 4 wherein said remote device is a radiofrequency power supply.

7. The assembly of claim 1 additionally comprising at least one temperature sensing device disposed on said flexible tip.

8. The assembly of claim 1 wherein said distal tip defines an exterior wall having at least one aperture therethrough.

9. The assembly of claim 8 wherein said at least one aperture is connected to a lumen defined in said flexible tip.

10. The assembly of claim 1 additionally containing at least one fiber optic cable disposed in said elongate member.

11. The assembly of claim 1 wherein said flexible tip is capable of deflecting in said second plane such that a distal end of said flexible tip physically contacts a more proximal portion of said assembly.

12. The assembly of claim 1 wherein said angle is between 90 and 180 degrees.

13. The assembly of claim 1 wherein said assembly additionally comprises a fluid irrigation system.

14. A deflectable surgical ablation assembly for forming ablations during open heart or open chest surgery, said assembly comprising:
   a main body comprising a rigid or semi-rigid elongate member defining a lumen and having a distal end and a proximal end, the member forming an angle at the distal end which defines a first plane of deflection;
   a multilumen flexible tip fixedly attached to said main body distal end, said tip comprising an active or non-active distal cap, said tip housing (1) a pull wire attached to a linear spring for deflecting the distal member about a second plane of deflection that is generally perpendicular to said first plane and (2) at least one electrode disposed on an outer surface of the tip; and
   a handle disposed at the proximal end of said main body for manipulating said pull wire, wherein said handle is rigidly connected to the main body and effective for transmitting axial forces applied by a surgeon to tissue being ablated.

15. The assembly of claim 14 additionally comprising a connector disposed on said handle for transmitting electromagnetic energy between said tip and a remote device.

16. The assembly of claim 15 wherein said remote device is an electrocardiogram recording system.

17. The assembly of claim 15 wherein said remote device is a radiofrequency power supply.

18. The assembly of claim 14 additionally comprising at least one temperature sensing device disposed on said flexible tip.

19. The assembly of claim 14 wherein said distal tip defines an exterior wall having at least one aperture therethrough.

20. The assembly of claim 19 wherein said at least one aperture is connected to a lumen defined in said flexible tip.

21. The assembly of claim 14 additionally containing at least one fiber optic cable disposed in said elongate member.

22. The assembly of claim 14 wherein said flexible tip is capable of deflecting in said second plane such that a distal end of said flexible tip physically contacts a more proximal portion of said assembly.

23. The assembly of claim 14 wherein said angle is between 90 and 120 degrees.

24. The assembly of claim 13 wherein said assembly additionally comprises a fluid irrigation system.

25. The deflectable surgical ablation assembly of claim 1, wherein the rigid or semi-rigid elongate member has a length of between about 4 and about 8 inches.

26. The deflectable surgical ablation assembly of claim 13, wherein the rigid or semi-rigid elongate member has a length of between about 4 and about 8 inches.

* * * * *